United States Patent
Arber et al.

(10) Patent No.: US 9,770,602 B2
(45) Date of Patent: *Sep. 26, 2017

(54) IMAGE GUIDED RADIATION THERAPY APPARATUS

(71) Applicant: Elekta AB (Publ), Stockholm (SE)

(72) Inventors: Philip Lee Arber, West Sussex (GB); Joseph Hubert Marie Habets, Oirsbeek (NL); Clifford William Perkins, West Sussex (GB); John Shelley, Surrey (GB)

(73) Assignee: Elekta AB (Publ), Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/078,392

(22) Filed: Mar. 23, 2016

(65) Prior Publication Data

US 2016/0220845 A1 Aug. 4, 2016

Related U.S. Application Data

(63) Continuation of application No. 14/524,660, filed on Oct. 27, 2014, now Pat. No. 9,333,375.

(30) Foreign Application Priority Data

Oct. 28, 2013 (GB) .................................. 1319001.2

(51) Int. Cl.
*A61N 5/10* (2006.01)
*G21K 1/02* (2006.01)
*G21K 1/04* (2006.01)

(52) U.S. Cl.
CPC ......... *A61N 5/1045* (2013.01); *A61N 5/1047* (2013.01); *A61N 5/1049* (2013.01);
(Continued)

(58) Field of Classification Search
None
See application file for complete search history.

(56) References Cited

U.S. PATENT DOCUMENTS 4,532,645 A * 7/1985 Morris ..................... A61B 6/06
                                                     248/674
4,880,985 A    11/1989 Jones
(Continued)

FOREIGN PATENT DOCUMENTS

CN    101211676 A    7/2008
JP    59-180476 A    10/1984
(Continued)

OTHER PUBLICATIONS

GB Search Report issued in corresponding Application No. GB 1319001.2, dated May 27, 2014, one (1) page.

*Primary Examiner* — Michael Logie
(74) *Attorney, Agent, or Firm* — Finnegan, Henderson, Farabow, Garrett & Dunner, LLP

(57) ABSTRACT

An IGRT apparatus comprising a medical imaging device (1) integrated with a linear accelerator (3, 4), the linear accelerator (3, 4) configured for emitting a radiation beam which is shaped by a beam shaper (8, 17), wherein the position of the beam shaper (8, 17) is adjustable between a first position and a second position, wherein the first position is a treatment position and the second position is a non-treatment position and wherein the IGRT apparatus comprises a gantry (2) and wherein the first position is within the gantry (2) and the second position is removed from the gantry (2).

20 Claims, 4 Drawing Sheets

(52) U.S. Cl.
CPC ............ *A61N 5/1067* (2013.01); *G21K 1/02* (2013.01); *G21K 1/04* (2013.01); *A61N 2005/1055* (2013.01); *A61N 2005/1056* (2013.01)

(56) References Cited

U.S. PATENT DOCUMENTS

| | | | |
|---|---|---|---|
| 5,189,687 | A | 2/1993 | Bova |
| 5,438,991 | A | 8/1995 | Yu et al. |
| 5,751,781 | A | 5/1998 | Brown et al. |
| 5,866,914 | A * | 2/1999 | Jones ............... G21K 1/02 250/505.1 |
| 6,459,769 | B1 | 10/2002 | Cosman |
| 7,741,624 | B1 | 6/2010 | Sahadevan |
| 2002/0150215 | A1 | 10/2002 | Barnes |
| 2008/0107239 | A1 | 5/2008 | Sayeh |
| 2008/0197304 | A1 | 8/2008 | Urano et al. |
| 2009/0001296 | A1 | 1/2009 | Kuduvalli |
| 2010/0239066 | A1 * | 9/2010 | Fahrig ............... A61N 5/1049 378/65 |
| 2011/0156703 | A1 * | 6/2011 | O'Connor ............ A61N 5/1049 324/307 |
| 2011/0201919 | A1 * | 8/2011 | Allen ................ A61N 5/1042 600/411 |
| 2011/0210261 | A1 | 9/2011 | Maurer, Jr. |
| 2012/0203490 | A1 | 8/2012 | Sayeh et al. |
| 2013/0035586 | A1 | 2/2013 | Knox et al. |
| 2013/0221243 | A1 | 8/2013 | Perkins |
| 2014/0010355 | A1 * | 1/2014 | Seeber .................. G21K 1/04 378/152 |
| 2014/0037062 | A1 | 2/2014 | Daniel Elgort |
| 2014/0275963 | A1 * | 9/2014 | Shvartsman ........... A61B 5/055 600/411 |

FOREIGN PATENT DOCUMENTS

| | | | |
|---|---|---|---|
| JP | 59180476 A | * 10/1984 | ............ G01T 1/161 |
| WO | WO 03/008986 A2 | 1/2003 | |

* cited by examiner (a)

(b)

IMAGE GUIDED RADIATION THERAPY APPARATUS

CROSS REFERENCE TO RELATED APPLICATION

This is a continuation of application Ser. No. 14/524,660, filed Oct. 27, 2014, and claims the benefit of GB 1319001.2, filed on Oct. 28, 2013, both of which are incorporated herein by reference.

FIELD OF THE INVENTION

The present invention relates to image guided radiation therapy (IGRT) apparatus. More particularly the invention provides an IGRT apparatus in which components can be conveniently and efficiently maintained and repaired.

BACKGROUND OF THE INVENTION

Radiation therapy is a localised treatment designed to treat an identified tissue target (such as a cancerous tumour) and spare the surrounding normal tissue from receiving doses above specified tolerances thereby minimising risk of damage to healthy tissue. Prior to delivery of radiation therapy, an imaging system can be used to provide a three dimensional image of the target from which the target's size and mass can be estimated and an appropriate treatment plan determined.

Many factors may contribute to differences between the dose distribution determined in the treatment plan and the delivered dose distribution. One such factor is an inconsistency between the patient position at the imaging stage and the patient position in the radiation treatment unit.

Image guided radiation therapy (IGRT) is known. The method involves the use of an imaging system to view target tissues whilst radiation treatment is being delivered to the target tissue. IGRT incorporates imaging coordinates from the treatment plan to ensure the patient is properly aligned for treatment in the radiation therapy device.

Various medical imaging technologies are used to identify target tissues in radiation therapy planning and IGRT. These include (without limitation); Computed Tomography (CT), Positron Emission Tomography (PET) and Magnetic Resonance Imaging (MRI). MRI is ideal for on-line position verification during radiotherapy, it is able to make fast 2D images of soft tissues with orientation along and perpendicular to the field axis, allowing imaging at critical locations which are defined during the treatment planning procedure. MRI also provides excellent contrast between tissue types giving a sharp image of the target.

The Applicant's prior published international patent application no. WO03/008986 describes a device for use in IGRT which includes the functions of an MRI device in a radiation therapy treatment apparatus and proposes technology for overcoming the problems in doing so.

The large scale of these combined devices will be appreciated. Such devices are typically of the order of 2-3 meters in diameter and they weigh several tons. It will be appreciated they cannot be easily transported or manoeuvred for maintenance and repair.

SUMMARY OF THE INVENTION

In accordance with the present invention there is provided an image guided radiation therapy apparatus comprising a medical imaging device integrated with a linear accelerator, the linear accelerator configured for emitting a radiation beam which is shaped by a beam shaper, wherein the position of the beam shaper is adjustable between a first position and a second position wherein the first position is a treatment position and the second position is a non-treatment position.

The inventors have recognised that the cumbersome proportions of a combined medical imaging and radiation therapy treatment device present maintenance and repair engineers with a challenge in accessing component parts of the device for service.

Preferably, the second position is a service position.

Preferably, the IGRT apparatus comprises a gantry and the first position is within the gantry and the second position is removed from the gantry.

Whilst the beam shaper component must be carefully aligned for treatment, its position within the gantry is inconvenient for the purposes of servicing. As one of the more complex components of the apparatus, it is important the beam shaper can be readily accessible for maintenance purposes. The provision of adjustment means for adjusting the position of the beam shaper enables the beam shaper to be moved between an operational position and a service position, the service position being much more easily accessible for the service engineer. Optionally, the device provides for a range of servicing positions.

Preferably, the position of the linear accelerator is moveable with the beam shaper between the first and second positions.

The radiation beam emitter of the linear accelerator is transported around the target tissue by means of a gantry. When in operation, the beam shaper must be positioned adjacent the radiation beam emitter within the gantry.

The beam shaper is typically a multi-leaf collimator (MLC). MLC comprises multiple inter-engaging metal leaves which can each be moved independently by means of multiple electro-mechanical positioning mechanisms.

The medical imaging device is desirably an MRI device. Since such devices generate a very strong magnetic field it is advantageous to distance a predominantly metal component such as an MLC from the magnetic field for servicing since any ferromagnetic material in the MLC will be drawn to the magnetic field potentially resulting in damage or disassembly of sub-components.

Adjustment of the beam shaper position can be achieved by means of an adjustment arm to which the beam shaper is mounted and a linkage connecting the adjustment arm to a fixed body and operable to move the beam shaper between the first and second position. For example, the fixed body might be the wall, floor or ceiling of a room in which the IGRT apparatus is installed. Alternatively the fixed body might comprise a support beam fixed to any of the walls, floor or ceiling of a room in which the IGRT apparatus is installed. In another alternative, the fixed body is a gantry or framework of the IGRT apparatus itself.

The adjustment arm may be adjusted manually or by a mechanical or electro-mechanical actuation means.

In some embodiments the linkage comprises a pivot operable to pivot the beam shaper from a position within the gantry to a position removed from the gantry.

In such embodiments, the beam shaper can be caused to travel through a simple arc from the first to the second position and desirably also in reverse from the second back to the first position. The pivot can comprise a simple hinge located at or adjacent a first end of the adjustment arm distal from a second end to which the beam shaper is mounted.

Actuation means may comprise any conventional mechanical or electro-mechanical means; for example (but without limitation) a hydraulic or pneumatic system may be used. In another alternative, one or more electrically operated actuators may be used. The actuators may comprise rotary actuators, linear actuators or a combination thereof. The actuation means may further comprise a gearing system to facilitate leverage of the heavy components. Actuation means may be removably attachable to the adjustment arm or may form an integral part of the arm.

In more complex embodiments, the linkage may comprise a multi-axis joint. A multi-axis joint allows the arm to be pivoted as described above but also permits rotation of the adjustment arm about its own axis allowing greater manoeuvrability in positioning the beam shaper for servicing.

The adjustment arm may be provided with one or more joints operable to present the beam shaper in an increased number of positions and orientations. Joints in the adjustment arm may comprise simple hinge joints, multi-axis joints or any combination thereof.

The adjustment arm may incorporate a linear actuator allowing the length of the arm to be adjusted thereby providing further flexibility in the positioning of the beam shaper when removed from the gantry.

A variety of potential configurations for IGRT apparatus in accordance with the invention are possible. For example, the imaging device could be an MRI device of an open ring configuration or a drum configuration. An open system may require more sophisticated engineering but may provide benefits to the subject in providing for less intimidating, more comfortable treatment. In such a design, an open ring MRI system is integrated with a rotating linear accelerator mounted on an additional ring. The additional ring may also support a beam stopper and a megavoltage imaging system.

Preferably the apparatus is configured such that magnetic imaging device and the linear accelerator may be operated both independently and simultaneously.

Desirably the magnetic imaging device and linear accelerator are arranged to share an isocentre.

A preferred and probably more economical design solution may use a dosed drum design based on the conventional drum MRI design.

Active or passive magnetic shielding in the integrated system may provide a minimal field strength at the mid plane around the MRI magnet. This shielding can prevent magnetic distortion of the accelerator tube and will also assist in minimising disturbance of the other accelerator systems in the dose proximity of the MRI system. Inclusion of the shielding results in a system necessarily of wider diameter than a conventional system and thus in a larger distance between isocentre and focus. Alternatively the magnets can be designed in order to minimise the field strength at the point(s) in space where the accelerator will operate.

Preferably, the IGRT apparatus comprises a light source for projecting a light beam through the beam shaper when the beam shaper is in the second position. This can be used to confirm configuration and correct working of the beam shaper during servicing. For example, the light beam can be projected onto a ceiling or other surface.

Preferably, the linear accelerator is positioned such that the path of radiation from the linear accelerator to a patient is linear. Put another way, it is preferred that the path of radiation is not bent; rather the radiation path passes directly from the linear accelerator, through the beam shaper and to the patient.

An embodiment of the invention will now be described with reference to the accompanying figures.

DETAILED DESCRIPTION OF DRAWINGS

Figure 1:
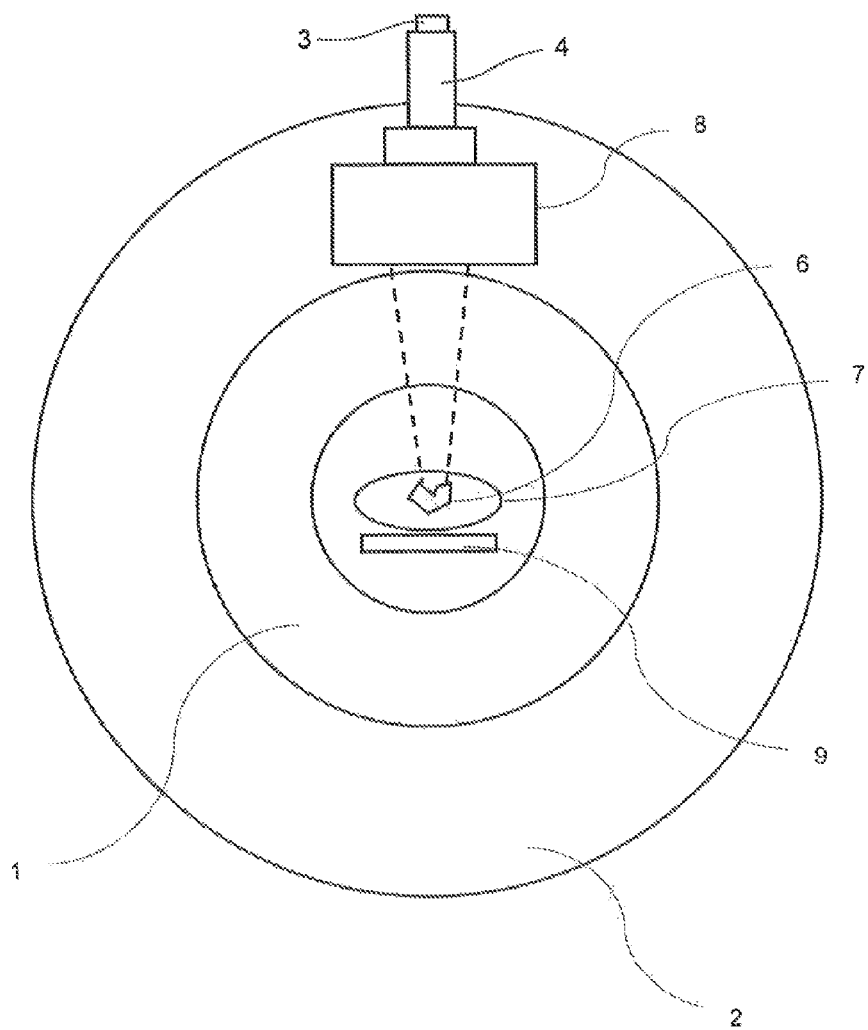
FIG. 1 shows schematically an IGRT apparatus.

As can be seen from FIG. 1, an integrated device is provided in a dosed drum arrangement which comprises an inner MRI portion 1 and an outer gantry portion 2 which incorporates the linear accelerator having a head including a radiation gun 3, acceleration tube 4 and an X-ray emission target (not shown). The resultant radiation is used to bombard a target 6 in a body 7 contained in the bore of the gantry portion 2. A beam shaper 8 uses data from the MRI to focus the radiation beam emitted by the linear accelerator onto the target 6. The body 7 is introduced to and guided through the isocentre on a sliding table 9. In use, the gantry is rotated about the isocentre to enable bombardment of the target 6 from multiple directions. The table 9 may also be tiltable to expose the target 6 to the direct line of the emitted beam in another plane.

Figure 2:
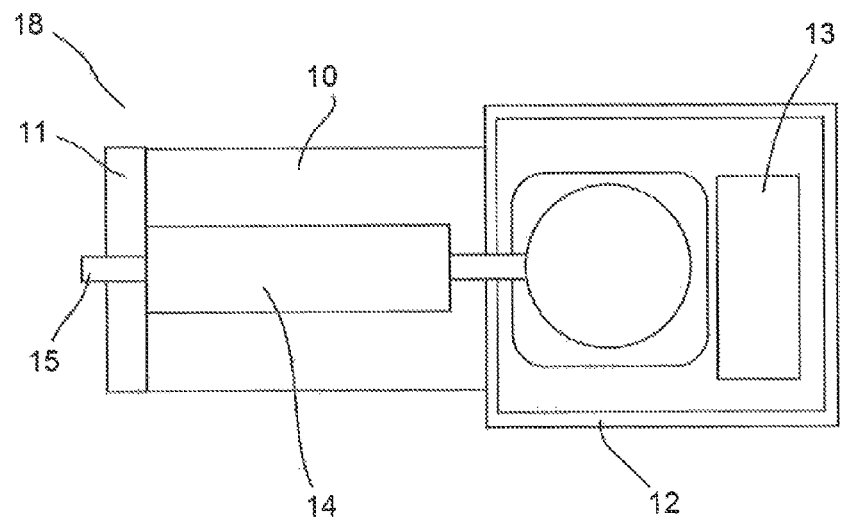
FIG. 2 shows in two orthogonal views (a) and (b), a beam shaper mounted on an adjustment arm and accompanying actuation means for actuating the adjustment arm in accordance with one embodiment of the invention.
Figure 2:
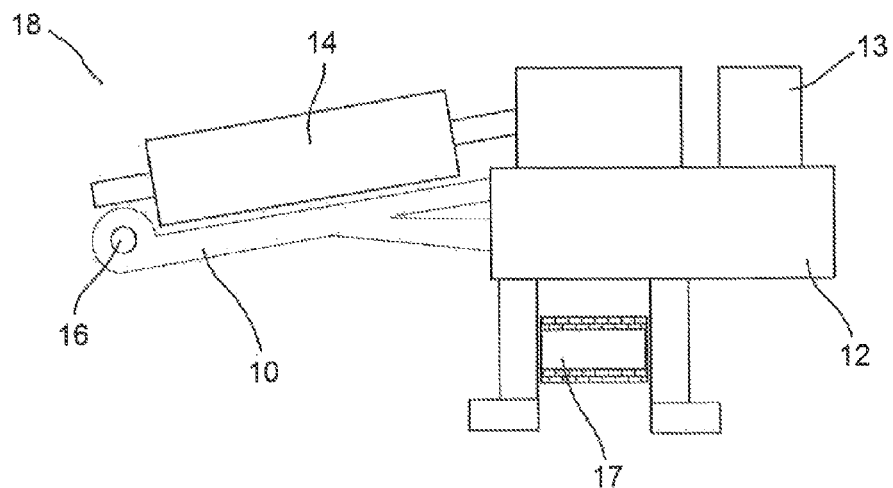

FIG. 2 shows two orthogonal views of an adjustment arm 18 which comprises a mechanical arm 10 having a first end 11 which can be connected to a framework in the gantry of a suitably arranged IGRT apparatus by means of a pivotal linkage passing through a bore 16 passing through the end 11. A second end of the arm 10 embodies a housing 12 which houses an MLC having a leaf driving section 13 and multiple leaf section 17. An actuator 14 is operable to cause the mechanical arm 10 to rotate about a pivot point at the centre of bore 16. The assembly is powered by cabling 15.

Figure 3:
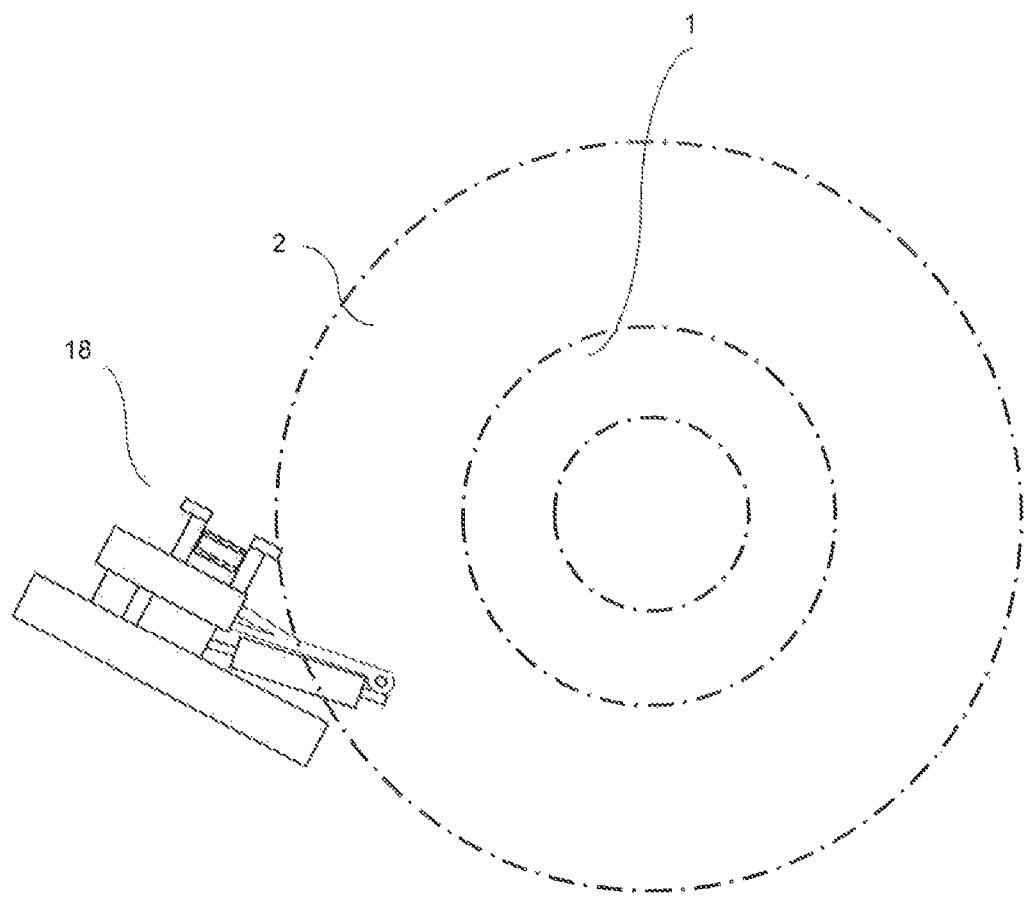
FIG. 3 shows the components of FIG. 2 arranged in an IGRT apparatus in accordance with an embodiment of the invention.

FIG. 3 shows schematically an adjustment arm 18 pivotally mounted in the gantry portion of an IGRT apparatus of substantially similar design to the apparatus shown in FIG. 1.

When it is desired to access the MLC 17 for maintenance or repair, the gantry is rotated to position the MLC at an appropriate height for the service engineer. One suitably positioned, the actuator 14 is operated to rotate the mechanical arm about the pivotal linkage through bore 16 allowing the assembly to be tilted outside of the outer circumference of the gantry 2 and the MLC revealed to the engineer in a safe and convenient position a good radial distance from the magnetic field present in the MRI portion 1.

Desirably the assembly is lockable in position in the gantry when radiation treatment is being delivered. This may be achieved by incorporating a locking mechanism into the actuator or linkage. In an alternative, a lockable panel is provided on an outer circumference of the gantry 2 for containing the assembly 18 during delivery of radiation treatment.

Figure 4A:
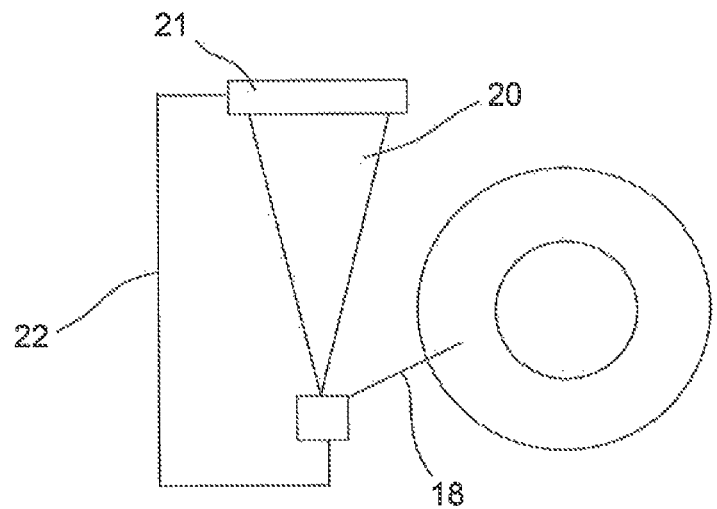
FIGS. 4a and 4b show the inclusion of a light source for projecting a light beam through the beam shaper.
Figure 4B:
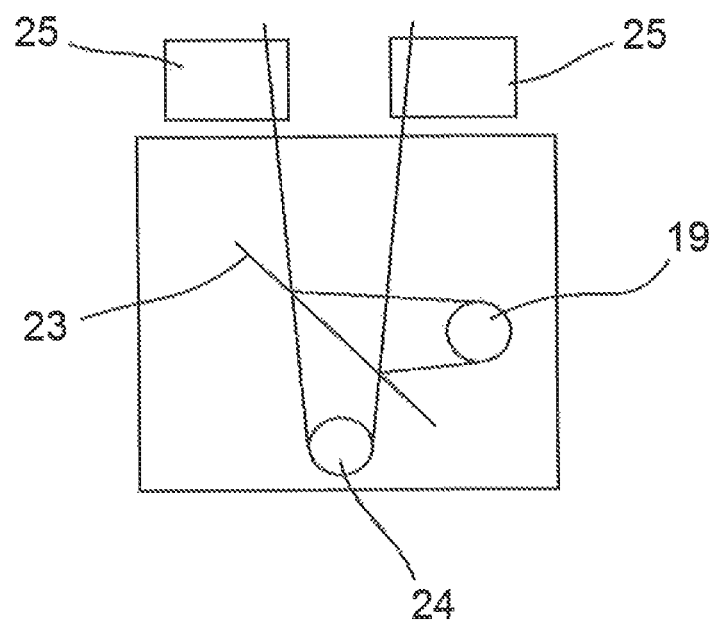

With reference to FIGS. 4a and 4b, the IGRT apparatus may include a light source 19 for projecting a light beam 20 through the beam shaper when the beam shaper is in the second position. This can be used to confirm configuration and correct working of the beam shaper during servicing. For example, the light beam 20 can be projected onto a detector 21 which is connected to calibration circuitry 22.

With particular reference to FIG. 4b, the light source 19 is bounced off a mirror 23 so that it follows the same path as radiation from the radiation source 24 through the leaves 25 of the MLC.

As will be evident from FIG. 4b, the radiation source is provided in line with the subject to be treated such that there is no need for a bending magnet.

Other embodiments and simple design variations of the embodiments disclosed herein will no doubt occur to the skilled addressee without departing from the true scope of the invention as defined in the appended claims.

The invention claimed is:

1. An image-guided radiation therapy (IGRT) apparatus, comprising:
   a medical imaging device integrated with a linear accelerator, the linear accelerator configured for emitting a radiation beam which is shaped by a beam shaper; and
   a gantry configured to rotate the emitted radiation beam about an axis,
   wherein the beam shaper is mounted to an adjustment arm configured to adjust the beam shaper between a first position and a second position, and
   wherein the medical imaging device is an MRI device generating a magnetic field, and the second position is a radial distance away from the magnetic field such that a magnetic field strength generated by the MRI device at the second position is lower than a magnetic field strength generated by the MRI device at the first position.

2. The IGRT apparatus as claimed in claim 1, wherein the first position is a treatment position, and the second position is a service position.

3. The IGRT apparatus as claimed in claim 1, wherein the position of the linear accelerator is moveable with the beam shaper between the first and second positions.

4. The IGRT apparatus as claimed in claim 1, wherein the beam shaper is a multi-leaf collimator.

5. The IGRT apparatus as claimed in claim 1, wherein the adjustment arm is connected to a fixed body through a linkage and operable to move the beam shaper between the first and second positions.

6. The IGRT apparatus as claimed in claim 5, wherein the fixed body is integral with the gantry, and wherein the linkage comprises a pivot operable to pivot the beam shaper from a position within the gantry to a position removed from the gantry.

7. The IGRT apparatus as claimed in claim 5, further comprising an actuator to move the adjustment arm between the first and second positions.

8. The IGRT apparatus as claimed in claim 7, wherein the actuator comprises a pneumatically or hydraulically operated component.

9. The IGRT apparatus as claimed in claim 8, wherein the actuator comprises at least one electro-mechanical actuator.

10. The IGRT apparatus as claimed in claim 9, further comprising a gearing system.

11. The IGRT apparatus as claimed in claim 5, wherein the linkage comprises a multi-axis joint.

12. The IGRT apparatus as claimed in claim 5, further comprising a locking mechanism for locking the beam shaper into position during delivery of radiation treatment.

13. The IGRT apparatus as claimed in claim 5, wherein the adjustment arm is provided with one or more joints operable to present the beam shaper in an increased number of positions and orientations.

14. The IGRT apparatus as claimed in claim 5, wherein the adjustment arm incorporates a linear actuator allowing the length of the arm to be adjusted thereby providing further flexibility in the positioning of the beam shaper when removed from the operational position.

15. The IGRT apparatus as claimed in claim 1, wherein the IGRT apparatus has a closed drum configuration.

16. The IGRT apparatus as claimed in claim 1, wherein the IGRT apparatus has an open ring configuration.

17. A radiation therapy apparatus for delivering radiation therapy to a target, the apparatus comprising:
   a linear accelerator configured to emit, via a radiation beam emitter, a radiation beam along a beam path toward the target;
   an imaging device configured to obtain an image of the target;
   a beam shaper configured to shape the emitted radiation beam emitted toward the target;
   a gantry coupled to the linear accelerator, wherein the gantry is configured to rotate the radiation beam emitter about an axis; and
   an adjustment arm connected to the gantry and to the beam shaper, wherein the adjustment arm is configured to adjust the beam shaper between a treatment position and a non-treatment position, and
   wherein the medical imaging device is an MRI device generating a magnetic field, and the non-treatment position is a radial distance away from the magnetic field such that a magnetic field strength generated by the MRI device at the non-treatment position is lower than a magnetic field strength generated by the MRI device at the treatment position.

18. The radiation therapy apparatus as claimed in claim 17, wherein the adjustment arm is connected to a fixed body through a linkage and operable to move the beam shaper between the treatment and non-treatment positions.

19. The radiation therapy apparatus as claimed in claim 18, wherein the fixed body is integral with the gantry, and wherein the linkage comprises a pivot operable to pivot the beam shaper from a position within the gantry to a position removed from the gantry.

20. The radiation therapy apparatus as claimed in claim 17, wherein the imaging device has an open ring configuration.

* * * * *